United States Patent [19]

Priem et al.

[11] 4,075,023
[45] Feb. 21, 1978

[54] POLYMERIZABLE UNSATURATED OXAZOLIDINES AND TETRAHYDRO-1,3-OXAZINES AND POLYMERS THEREOF

[75] Inventors: Jan Josef Priem, Mortsel; Walter Frans De Winter, Berchem, both of Belgium

[73] Assignee: AGFA-GEVAERT N.V., Mortsel, Belgium

[21] Appl. No.: 316,511

[22] Filed: Dec. 19, 1972

[30] Foreign Application Priority Data

Dec. 20, 1971 United Kingdom ............... 59034/71

[51] Int. Cl.$^2$ ............................................. G03C 1/72
[52] U.S. Cl. ..................................... 96/114; 96/115 P; 250/316; 260/8; 526/260
[58] Field of Search ............ 96/115 P, 115 R, 114 R, 96/114.4; 260/88.3, 8; 250/316

[56] References Cited

U.S. PATENT DOCUMENTS

| | | | |
|---|---|---|---|
| 3,006,762 | 10/1961 | Dersch | 96/114 |
| 3,060,028 | 10/1962 | Dersch | 96/114 |
| 3,341,332 | 9/1967 | Nakajima et al. | 96/114 |
| 3,360,373 | 12/1967 | Schaller | 96/114 |
| 3,367,777 | 2/1968 | Altavilla | 96/114 |
| 3,421,896 | 1/1969 | Altavilla | 96/114 |
| 3,429,707 | 2/1969 | Nakajima et al. | 96/114 |
| 3,482,980 | 12/1969 | Hayakawa et al. | 96/114 |

*Primary Examiner*—Edward C. Kimlin
*Attorney, Agent, or Firm*—William J. Daniel

[57] ABSTRACT

Oxazolidines and tetrahydro-1,3-oxazines which are substituted with 3-acryloyl or 3-methacryloyl groups are prepared by adding to an excess of a ketone and in the presence of a hydrogen chloride acceptor, about equimolecular amounts of a 2- or 3-amino lower alkanol and of acryloyl chloride or methacryloyl chloride, heating the mixture, and eliminating the unreacted ketone by destillation. The ketone corresponds to the formula:

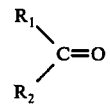

wherein
$R_1$ = alkyl (1-4 C),
$R_2$ = alkyl (1-4 C) or phenyl, or
$R_1$ and $R_2$ together represent the atoms necessary to complete an alicyclic group.

These unsaturated oxazolidines and tetrahydro-1,3-oxazines may be homo- or copolymerized, and these polymers may be used as plasticizers for gelatin, e.g. in photographic layers containing gelatin.

4 Claims, No Drawings

POLYMERIZABLE UNSATURATED OXAZOLIDINES AND TETRAHYDRO-1,3-OXAZINES AND POLYMERS THEREOF

The invention relates to a process for the preparation of polymerisable unsaturated oxazolidine and tetrahydro-1,3-oxazine monomers, to the polymerization of these unsaturated oxazolidine and tetrahydro-1,3-oxazine monomers, and to the monomers and polymers thus prepared.

According to the invention a process is provided for the preparation of oxazolidines or tetrahydro-1,3oxazines substituted with 3-acryloyl or 3-methacryloyl groups, which process comprises adding to an excess of a ketone and in the presence of a hydrogen chloride acceptor, approximatively equimolar amounts of a 2- or 3-amino lower alkanol and of acryloyl chloride or methacryloyl chloride and heating the mixture so as to effect a reaction, whereafter the unreacted ketone is eliminated by destillation, said ketone corresponding to the general formula:

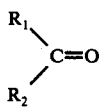

wherein:

$R_1$ represents an alkyl group of 1 to 4 carbon atoms;
$R_2$ represents an alkyl group of 1 to 4 carbon atoms or a phenyl group; or
$R_1$ and $R_2$ together with the carbon atom of the carbonyl group represent the atoms necessary to complete an alicyclic group.

The ketone is also used as solvent for the reaction mixture and is present in great excess, e.g. up to 10 times or even more the quantity of amino-alkanol and (meth)-acryloyl chloride present. Suitable ketones are e.g. acetone, methyl ethyl ketone, cyclohexanone, and acetophenone.

The term 2- or 3-amino lower alkanol is used for aminoalkanols, in which the amino group is present in the second or third position with respect to the hydroxyl group. For convenience sake all these 2- or 3-amino lower alkanols will be called aminoalkanols hereinafter.

Suitable aminoalkanols are e.g.:

| | |
|---|---|
| 2-aminoethanol | (274) |
| 1-amino-2-propanol | (289) |
| 1-amino-2-methyl-2-propanol | (292) |
| 2-amino-1-propanol | (E I 432) |
| 2-amino-2-methyl-1-propanol | (E III 783) |
| 3-amino-1-propanol | (288) |
| 1-amino-2-butanol | (292) |
| 2-amino-1-butanol | (291) |
| 3-amino-1-butanol | (E I 438) |
| 3-amino-2-butanol | (292) |
| 4-amino-2-butanol | (E III 782) |

The numbers between brackets refer to the pages of volume IV of "Beilsteins Handbuch der Organischen Chemie". When the numbers are preceded by E I or E III they refer to pages of the fourth volumes of the "Erstes Ergänzungswerk" or of the "Drittes Ergänzungswerk" respectively.

Sodium hydrogen carbonate is preferably added as hydrogen chloride acceptor, although other known hydrogen chloride acceptors such as pyridine, triethylamine, diethylaniline, and dimethylacetamide may also be used.

The aminoalkanol and the (meth)acryloyl chloride are added to the ketone in about equimolar amounts and preferably at room temperature. The best results are obtained when for 1 mole of aminoalkanol about 1.1 mole of (meth)acryloyl chloride is present.

First the sodium hydrogen carbonate is added to the ketone together with a small quantity of a polymerisation inhibitor such as copper curlings, followed by the aminoalkanol, whereafter the (meth)acryloyl chloride is added dropwise. One can also add the two latter compounds in the reverse order, i.e. first the (meth)acryloyl chloride and finally the aminoalkanol. Since the addition of the (meth)acryloyl chloride causes an exothermic reaction, it is advisable to cool the reaction mixture until the full amount of both compounds has been added. Thereafter, the reaction mixture is heated at a temperature generally not exceeding 100° C. Above this temperature and notwithstanding the polymerisation inhibitor added to the reaction mixture, an undesired polymerisation reaction might occur. When a ketone boiling below 100° C is used such as acetone, the reaction is heated conveniently at the reflux temperature of the ketone. When, however, a ketone boiling above 100° C is used, e.g. cyclohexanone, the mixture is heated at about 100° C.

Without limitation of the scope of the invention the following reaction scheme may be put forward, although the invention is not bound as to whether this reaction scheme is indeed followed in reality. When acetone, 2-aminoethanol and methacryloyl chloride are used as reaction components and sodium hydrogen carbonte is used as hydrogen chloride acceptor, the reaction scheme may be as follows:

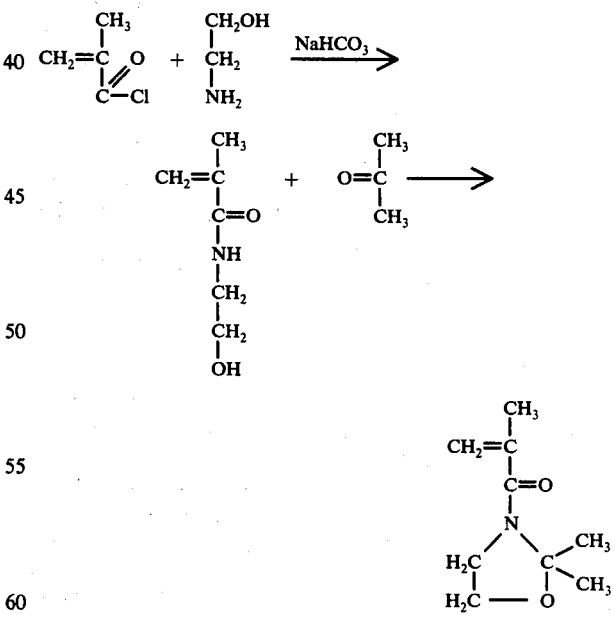

The polymerisable unsaturated monomer formed in this case is 2,2-dimethyl-3-methacryloyl-oxazolidine.

When a 3-aminoalkanol instead of a 2-amino-alkanol is added to the reaction mixture, a corresponding unsaturated tetrahydro-1,3-oxazine monomer will form.

The oxazolidines and tetrahydro-1,3-oxazines substituted with 3-acryloyl and 3-methacryloyl groups and prepared according to the process of the invention correspond to the general formulae:

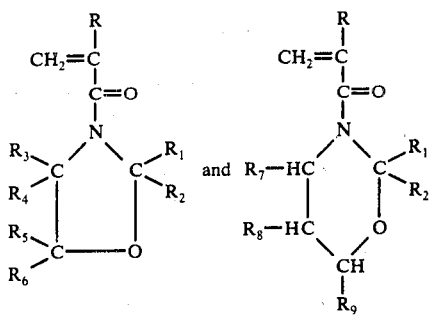

wherein:
R represents hydrogen or methyl,
$R_1$ represents an alkyl group of 1 to 4 carbon atoms,
$R_2$ represents an alkyl group of 1 to 4 carbon atoms or a phenyl group, or
$R_1$ and $R_2$ together represent the atoms necessary to complete an alicyclic group,
each of $R_3$, $R_4$, $R_5$, and $R_6$ represents hydrogen, methyl or ethyl, and
each of $R_7$, $R_8$, and $R_9$ represents hydrogen or methyl.

These structural formulae are confirmed by elemental nitrogen analysis and by the nuclear magnetic resonance spectra and infrared (N.M.R. and I.R.) spectra of the compounds obtained according to the reaction of the invention.

The unsaturated oxazolidines and tetrahydro-1,3-oxazines formed by the process of the invention can be polymerised and also copolymerised according to different polymerisation techniques, such as bulk, solution, suspension or emulsion polymerisation. Polymerisation can be initiated e.g. by free radicals that can be obtained by thermal decomposition of chemical initiators or by the action of a reducing agent on an oxidizing agent (redox initiators), by the physical action of ultraviolet radiation or other high energy radiation, e.g. ultrasonic waves, or other known polymerisation techniques, e.g. anionic or cationic polymerisation.

Most important chemical initiators are e.g. persulphates (sodium, potassium, and ammonium persulphate), hydrogen peroxide, 4,4'-azo-bis(4-cyanovaleric acid) and other compounds that are soluble in water; further azodiisobutyronitrile, benzoyl peroxide, chlorobenzoyl peroxide and other compounds that are insoluble in water. Suitable redox initiators are hydrogen peroxide iron(II) salt, potassium persulphate potassium hydrogen sulphite, cerium salt alcohol complexes, and the like.

A survey of the polymerisation initiators and of their influence can be found in "Emulsion Polymerisation", by F.A. Bovey et al, Interscience Publishers Inc., New York, 1953, p. 59-93.

When the unsaturated oxazolidines and tetrahydro-1,3-oxazines of the invention are copolymerised, they may be mixed with at least one polymerisable ethylenically unsaturated monomer such as styrene, acrylic acid esters, acrylonitrile, acrolein, and the like.

The homopolymers and copolymers can be used as plasticizers for gelatin e.g. in photographic layers containing gelatin. When mixed in latex form with aqueous gelatin solutions they form extremely clear and transparent layers upon drying, which layers remain fully transparent in wet as well as in dry state.

When mixed with gelatin in photographic layers they favourably improve the physical properties of these layers, especially the brittleness thereof and at the same time they have no influence at all on the photographic properties of these layers.

Although the description has been restricted to the reaction of a ketone with a 2- or 3-amino lower alkanol and an acryloyl chloride or methacryloyl chloride in the presence of a hydrogen chloride acceptor, it is evident that similar products will be obtained by replacing the ketone by an aldehyde.

The invention is illustrated by the following examples.

EXAMPLE 1

In a reaction flask equipped with a stirrer, a dropping funnel, a thermometer and a coller were introduced:

| | |
|---|---|
| anhydrous acetone | 2 l |
| sodium hydrogen carbonate | 252 g (3 mole) |
| 2-aminoethanol | 122 g (2 mole) |

A small amount of copper curlings was added as polymerisation inhibitor to the resulting mixture. The mixture was stirred while 230 g of freshly distilled methacryloyl chloride (2,2 moles) were added in 15 minutes at room temperature through the dropping funnel. By cooling with ice-water the temperature of the reaction mixture in the flask was maintained at about 30° C. After the addition of the methacryloyl chloride, stirring was continued for 15 minutes at room temperature after which the reaction mixture was heated for 1 hour on a boiling water-bath at reflux temperature (55° C). Subsequently, the reaction flask was cooled and the mixture filtered to eliminate the sodium hydrogen carbonate and precipitated salt. The odour characteristic of the acid chloride could no longer be observed. The filtered solution was evaporated in vacuo to eliminate the excess acetone. An orange-red, slightly viscous oil remained. After flash distillation followed by fractionation 190 g of a clear, colourless liquid was obtained which after cooling forms crystals melting at 18° C. The 2,2-dimethyl-3-methacryloyl-oxazolidine formed corresponds to the formula:

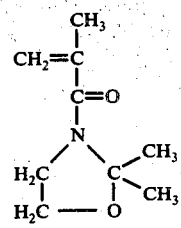

To prove that in the compound formed no primary amino group was present, the Rimini test was carried out. When according to this test 1 ml of pure acetone and 1 drop of a freshly prepared 1% aqeuos solution of sodium nitroprusside are added to a suspension or solution of one drop of a compound, a violet-red colour will develop within one minute if the compound contains a primary amino group. In this case the Rimini test gave a negative result so that it could be concluded that the original primary amino group of the 2-amino-ethanol had disappeared.

The 2,2-dimethyl-3-methacryloyl-oxazolidine had a boiling point of 60°-62° C at a pressure of 0.6 mm Hg. The refractive index showed to be 1.4665/25° C.

The structural formula given above was confirmed by N.M.R. analysis and by I.R. analysis. The mass spectrometer indicated a molecular weight of 154.08, which corresponds with the calculated value.

Nitrogen analysis gave the following results:

| calculated | : | 8.28 |
|---|---|---|
| found | : | 8.35 |

EXAMPLE 2

In a reaction flask as described in Example 1 the following compounds were introduced:

| anhydrous methyl ethyl ketone | 1 l |
|---|---|
| sodium hydrogen carbonate | 126 g (1.5 mole) |
| 2-aminoethanol | 61 g (1 mole) |

A few copper curlings were added as polymerisation inhibitor thereto. The mixture was cooled to about 0° C and 104.5 g of methacryloyl chloride (1 mole) were added in 15 minutes through the dropping funnel, whereafter stirring was continued for another 15 minutes. The mixture was then heated for 2 hours on a boiling waterbath at reflux temperature (80° C). Then the reaction mixture was cooled to room temperature and filtered. The remaining solution was evaporated in vacuo to eliminate the excess methyl ethyl ketone. An orange-red, slightly viscous oil remained. After flash distillation the monomer was fractionated again, whereby a small quantity of the monomer polymerised in the flask. The monomer itself was a colourless oil boiling at 80° C at a pressure of 1.5 mm Hg. It has a refractive index of 1.4662/25° C. The 2-methyl-2-ethyl-3-methacryloyl-oxazolidine formed corresponded to the formula:

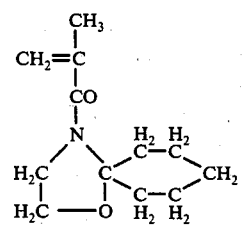

This structural formula was confirmed by N.M.R. and I.R. analysis. Vapour phase chromatography showed the purity of the compound to be more than 98%.

Elemental analysis gave the following results:
C calculated 65.55; found 65.80
H calculated 9.28; found 9.55
N calculated 7.65; found 7.50

EXAMPLE 3

In a reaction flask as used in Example 1 the following compounds were introduced:

| cyclohexanone | 1 liter |
|---|---|
| sodium hydrogen carbonate | 126 g (1.5 mole) |
| 2-aminoethanol | 61 g (1 mole) |

A small amount of copper curlings was added to this mixture. While stirring at room temperature 115 g of methacryloyl chloride (1.1 mole) were added through the dropping funnel. The temperature in the reaction flask was kept at about 30° C by cooling. The reaction mixture was heated for 2 hours at 100° C on a boiling water-bath whereafter the mixture was cooled at room temperature and filtered. The characteristic odour of an acid chloride had completely disappeared. The excess cyclohexanone was evaporated in vacuo. An orange-red slightly viscous oil remained, which on cooling crystallised.

The product was further purified by recrystallisation from a mixture of ethanol and water. White crystals were formed having a melting point of 70° C. The 2,2-pentamethylene-3-methacryloyl-oxazolidine formed corresponded to the formula:

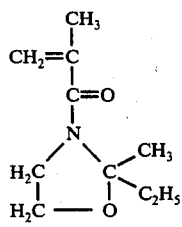

which was confirmed by N.M.R. and I.R. analysis. By mass spectrometry the molecular weight was found to be 209, which value corresponds to the calculated value. With thin layer chromatography none of the starting products could be found in the monomer finally obtained.

Elemental analysis gave the following results:
C calculated 68.9; found 68.96
H calculated 9.1; found 9.29
N calculated 6.7; found 6.65

EXAMPLE 4

In a reaction flask the following compounds were introduced:

| acetone | 1 l |
|---|---|
| sodium hydrogen carbonate | 126 g (1.5 mole) |
| 3-aminopropanol | 59 g (1 mole) | together with a few copper curlings. While stirring and keeping the temperature within the flask at approximately 30° C by cooling, 115 g of freshly distilled methacryloyl chloride were added through a dropping funnel. The reaction mixture was then refluxed for 2 hours on a boiling water-bath. After cooling the precipitate was filtered off. The filtrate was evaporated in vacuo. An orange-red liquid remained. After a first distillation there were formed: the main fraction at 72°-110° C/0.3 mm, a second fraction at 110°-140° C/0.3 mm, and a small amount of polymerised product remaining in the flask. The main fraction was distilled once more at a constant temperature of 78° c/1.5 mm. The 2,2-dimethyl-3-methacryloyl-tetrahydro-1,3-oxazine obtained had a refractive index of 1.4723/25° C and corresponded to the structural formula:

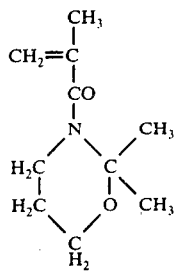

which formula was confirmed by N.M.R. and I.R. analysis.

Elemental analysis gave the following results:
C calculated 65.55; found 65.45
H calculated 9.28; found 9.50
N calculated 7.65; found 7.55

EXAMPLE 5

In a reaction flask as in Example 1 the following compounds were introduced:

| anhydrous acetone | 2 l |
|---|---|
| sodium hydrogen carbonate | 252 g (3 mole) |
| 1-amino-2-propanol | 150 g (2 mole) | together with a few copper curlings as polymerisation inhibitor. The mixture was stirred while adding in 15 minutes at room temperature through a dropping funnel 230 g of freshly distilled methacryloyl chloride (2.2 mole). Since the reaction was exothermic cooling was necessary. The mixture was then refluxed for 3 hours (55°–56° C), whereafter the mixture was cooled. The precipitate in the flask was filtered off. The filtrate was evaporated in vacuo. The remaining yellow slightly viscous oil was fractionated. 2,2-dimethyl-3-methacryloyl-5-methyl-oxazolidine was obtained upon destillation at 62°–64° C/0.8 mm. It had a melting point of 24° C and a refractive index of 1.4610/25° C and corresponded to the formula:

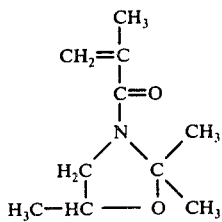

This structural formula was confirmed by N.M.R. and I.R. analysis. Vapour phase chromatography indicated a purity of about 96%.

Elemental analysis gave the following results:
C calculated 65.55; found 65.45
H calculated 9.28; found 9.45
N calculated 7.65; found 7.30

EXAMPLE 6

5 g of 2,2-dimethyl-3-methacryloyl oxazolidine (of Example 1), 50 g of ethanol, and 25 mg of azodiisobutyronitrile were introduced in a pressure tube. The pressure tube was rinsed with nitrogen, sealed, and then heated at 60° C for 60 hours. The mixture became turbid. The pressure was opened and the polymer was precipitated by the addition of dimethyl ether. The precipitate was filtered and washed with dimethyl ether. The polymer was insoluble in methylene chloride, hexane, ethyl acetate, ether, cyclohexanone, carbon tetrachloride, and ethylene glycol monomethyl ether, and is partially soluble in water, dimethylformamide and methanol.

EXAMPLE 7

In a reaction flask provided with a stirrer, a contact thermometer, 2 dropping funnels and a cooler 275 ml of demineralised water and 3 g of the sodium salt of oleyl-methyltauride were introduced. The flask was rinsed with nitrogen and heated at 90° C.

A mixture of 30 g of 2,2-dimethyl-3-methacryloyloxazilidine (Example 1) and 30 g of butyl acrylate was introduced through the first dropping funnel. Through the second dropping funnel were introduced 300 mg of the sodium salt of 4,4'-azo-bis(cyanovaleric acid) and 25 ml of demineralised water.

One fourth of the content of each dropping funnel was introduced into the reaction flask and after 5 minutes the remainders of both solutions were added within 30 minutes. Polymerisation was continued for 2 hours, whereafter the latex formed was cooled. Yield: 340 ml of a clear latex, free of precipitated substances and having a concentration of 13.5% by weight. Upon isolation a soft, rubber-like copolymer was obtained. Nitrogen analysis gave 2.58% by weight of nitrogen, which corresponds to 31% by weight of 2,2-dimethyl-3-methacryloyl-oxazolidine present in the copolymer.

An aqueous solution of gelatin having a concentration of 8% was mixed with the above latex so that 25% by weight of copolymer was present with respect to dry gelatin. This mixture could be applied as a layer e.g. on a cellulose triacetate film. After drying a completely transparent and clear layer was formed. The addition of the copolymer to gelatin did not impair the physical properties of the gelatin layer, so that the copolymer could be used as a partial substitute for gelatin in photographic layer containing gelatin.

EXAMPLE 8

In a reaction flask equipped with a stirrer a contact thermometer and a reflux condenser 25 ml of benzene free of thiophene, 5 g of freshly distilled styrene and 5 g of 2-methyl-2-ethyl-3-methacryloyloxazolidine (Example 2) were introduced. The mixture was rinsed with a stream of nitrogen and heated at 70° C. At this temperature 100 mg of azo-bis-isobutyronitrile were added. Polymerisation was continued at 70° C for about 24 hours whereafter another 100 mg of azo-bis-isobutyronitrile were added. Total reaction time: 48 hours. The copolymer was isolated from solution by pouring in an excess of hexane.

Yield: 4.4 g of copolymer having an intrinsic viscosity at 25° C in methylene chloride of 0.072 dl/g. Analysis showed a 1.7% by weight content of nitrogen, which corresponds with 44.4% by weight of 2-methyl-2-ethyl-3-methacryloyl-oxazolidine.

EXAMPLE 9

In a reaction flask as described in Example 8 25 ml of benzene free of thiophene, 9 g of freshly distilled styrene, 1 g of 2-methyl-2-ethyl-3-methacryloyl-oxazolidine (Example 2) and 100 mg of azobisisobutyronitrile were introduced.

Polymerisation proceeded at 70° C for 24 hours. The copolymer formed was isolated by pouring the reaction mixture in an excess of hexane. Yield: 5.15 g of copolymer having an intrinsic viscosity at 25° C in methylene chloride of 0.08 dl/g. Analysis showed a 0.75% by weight content of nitrogen corresponding to the presence of 10% by weight of oxazolidine monomer.

EXAMPLE 10

In a reaction flask as in Example 7 were introduced 275 ml of demineralised water and 3 g of the sodium salt of oleylmethyltauride. The mixture was stirred until dissolution while the flask was rinsed with nitrogen. The solution was then heated at 90° C.

30 g of 2,2-pentamethylene-3-methacryloyl-oxazolidine (Example 3) and 30 g of butyl acrylate were introduced in a first dropping funnel. The second dropping funnel contained 25 ml of demineralised water, into which 300 mg of the sodium salt of 4,4'-azo-bis(cyanovaleric acid) had been dissolved.

One fourth of the contents of both dropping funnels were introduced at once, and after 10 minutes the remaining amounts of monomer and of initiator solutions were added dropwise within about 5 minutes. The mixture was left to polymerise for 2 hours. The latex formed was freed from residual monomer by evaporation at 90° C under slightly reduced pressure.

Upon cooling a clear, easily filterable latex free of any coagulate and having a concentration of 14.6% by weight was obtained. The isolated copolymer had a rubber-like aspect and was slightly tacky. It had an intrinsic viscosity at 25° C in methylene chloride of 0.278 dl/g. Analysis showed a nitrogen content of 3.10% by weight, thus proving that the copolymer contained 46.8% by weight of 2,2-pentamethylene-3-methacryloyl-oxazolidine.

5 ml of the above latex at 40° C were added slowly with stirring to 10 ml of a 10% by weight aqueous solution of gelatin at 40° C. 5 ml of water at 40° C was added also. The solution obtained was coated on a glass plate and dried in the air. A completely homogeneous and very clear transparent film was formed comprising 50% by weight of gelatin and 50% by weight of copolymer.

EXAMPLE 11

In a reaction flask equipped with a stirrer, a reflux condenser and a contact thermometer 25 ml of anhydrous acetone, 5 g of freshly distilled methyl methacrylate and 5 g of 2,2-dimethyl-3-methacryloyltetrahydro-1,3-oxazine (Example 4) were introduced.

The mixture was heated at 70° C and 10 mg of azo-bis-isobutyronitrile was added. After polymerisation for 24 hours at 70° C another 100 mg of initiator were added. Total polymerisation time: 48 hours at 70° C. The copolymer was isolated by pouring the reaction mixture in an excess of water. Yield: 4.8 g of copolymer having an intrinsic viscosity in methylene chloride at 25° C of 0.078 dl/g. Analysis proved a nitrogen content of 1.4% by weight corresponding with a content of 18.3% by weight of 2,2-dimethyl-3-methacryloyltetrahydro-1,3-oxazine.

EXAMPLE 12

The process of Example 11 was repeated with the following reaction components: 25 ml of benzene free of thiophene and water, 9 g freshly distilled styrene, 1 g of 2,2-dimethyl-3-methacryloyl-tetrahydro-1,3-oxazine and 100 mg of azo-bis-iso-butyronitrile.

The copolymer formed was isolated by pouring into hexane. Yield: 4.53 g copolymer having an intrinsic viscosity at 25° C in methylene chloride of 0.114 dl/g and having a nitrogen content of 0.6% by weight, corresponding with 7.85% by weight of 2,2-dimethyl-3-methacryloyl-tetrahydro-1,3-oxazine.

EXAMPLE 13

The process of Example 7 was repeated with the following monomers: 30 g of 2,2-dimethyl-3-methacryloyl-5-methyl-oxazolidine (Example 5) and 30 g of styrene.

A clear latex was formed having a concentration of 17% by weight. The copolymer isolated from the latex was insoluble in all common organic solvents. This copolymer had a nitrogen content of 2.6% by weight corresponding with 34% by weight of oxazolidine monomer.

When the latex was mixed with aqueous gelatin solutions, films could be obtained that are very clear in wet as well as in dry state.

EXAMPLE 14

In a reaction flask equipped as described in Example 7 130 ml of demineralised water and 1.5 g of the sodium salt of oleylmethyltauride were introduced. The flask was rinsed with nitrogen and heated at 90° C. In the first dropping funnel 15 g of 2,2-dimethyl-3-methacryloyl-5-methyl-oxazolidine (Example 5) and 15 g of butyl acrylate were introduced. In the second dropping funnel 3 ml of a 5% aqueous solution of the sodium salt of 4,4'-azo-bis(cyanovaleric acid) were added and water up to 10 ml.

One fourth of the contents of both dropping funnels was added to the solution in the flask. Polymerisation started after about 5 minutes, whereafter the remaining contents of both funnels were dropped simultaneously into the flask within 15 minutes. After 1 hour of polymerisation at 95° C another 1.5 ml of the 5% aqueous initiator solution was added and polymerisation continued for 2 hours. The latex formed was then cooled and residual monomer was evaporated under slightly reduced pressure.

Yield: 135 ml of latex, practically free of precipitated substances and having a concentration of 17.7% by weight.

Analysis showed the copolymer to have a nitrogen content of 2.57% by weight corresponding to a 33.6% by weight content of oxazolidine monomer.

The latex formed is miscible with gelatin and extremely clear layers could be formed, which remained clear in wet as well as in dry state.

EXAMPLE 15

In a pressure vessel were introduced:

| | | |
|---|---|---|
| demineralised water | 640 | ml |
| sodium salt of oleylmethyl-tauride | 12.8 | g. |
| potassium persulphate | 1.6 | g |
| ethyl acrylate | 120 | g |
| 2,2-dimethyl-3-methacryloyl-oxazolidine | 32 | g |
| freshly distilled acrolein | 8 | g |

The pressure vessel was closed and polymerisation was allowed for 2 hours with stirring at a temperature of 75° C. The reaction was slightly exothermic. The mixture was cooled so that the temperature could not rise beyond approximately 85° C. The maximum pressure was 1.5 kg/sq.cm. After cooling the pressure vessel was opened. Yield: 790 ml of easily filterable latex containing no coagulant, having a pH of 3.52 and a concentration of 17% by weight.

The separated copolymer was insoluble in most of the common organic solvents. Analysis showed that the copolymer comprised 25.8% by weight of 2,2-dimethyl-3-methacryloyl-oxazolidine besides units deriving from ethyl acrylate and acrolein.

The latex was miscible with aqueous gelatin solutions. Extremely clear, transparent films could be formed from this mixture. These films remain transparent in wet as well as in dry state.

In a light-sensitive photographic film material for X-ray photography an antistress layer was coated on the silver halide emulsion layer. This layer was formed from an aqueous solution of gelatin, to which the above latex of copolymer had been added in such a way that 25% by weight of copolymer was present in respect of the weight of dry gelatin.

The physical properties of the photographic film material obtained were improved considerably, especially the resistance to abrasion and to pressure marks, which is very interesting when the photographic film material is treated in a rapid processing system. Further, the photographic properties such as fog, sensitivity and gamma were not impaired.

EXAMPLE 16

5 g of 2,2-dimethyl-3-methacryloyl-oxazolidine (of Example 1) were dissolved in 50 ml of anhydrous ether and cooled to −75° C. Three drops of boron trifluoride etherate were added as polymerization initiator. After standing for 24 hours at −75° C the mixture was heated at room temperature. A slightly coloured solution and a very thick viscous precipitate was formed. After evaporation of the liquid 4.2 g of light-brown, transparent glassy polymer was obtained. This polymer was soluble in boiling dimethylformamide and in water, but insoluble in methanol, tetrahydrofuran and acetone.

We claim:

1. A gelatin layer comprising gelatin and up to 50% by weight of the amount of dry gelatin present of a homopolymer of a vinyl monomer corresponding to one of the general formulae:

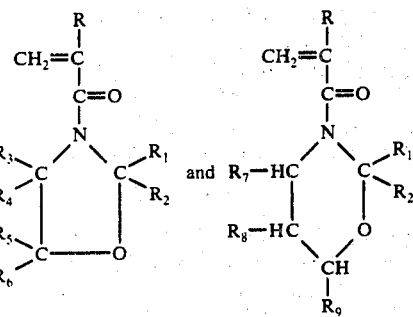

wherein:
R represents hydrogen or methyl,
$R_1$ is a $C_1$-$C_4$ alkyl group and $R_2$ is a $C_1$-$C_4$ alkyl group or a phenyl group, each of $R_3$, $R_4$, $R_5$ and $R_6$ represents a hydrogen atom, a methyl group, or an ethyl group, and
each of $R_7$, $R_8$ and $R_9$ represents a hydrogen atom or a methyl group.

2. A gelatin layer according to claim 1, wherein said gelatin layer forms part of a photographic light-sensitive material.

3. A gelatin layer comprising gelatin and up to 50% by weight of the dry gelatin present therein of a comonomer of a vinyl monomer corresponding to one of the general formulae:

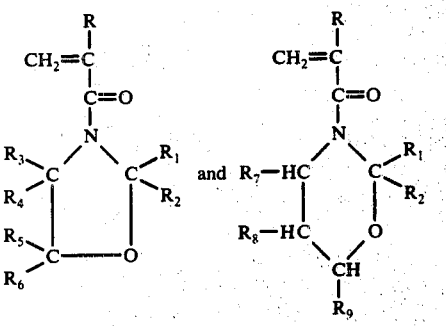

wherein:
R represents hydrogen or methyl,
$R_1$ is a $C_1$-$C_4$ alkyl group and $R_2$ is a $C_1$-$C_4$ alkyl group or a phenyl group,
each of $R_3$, $R_4$, $R_5$ and $R_6$ represents a hydrogen atom, a methyl group, or an ethyl group, and
each of $R_7$, $R_8$ and $R_9$ represents a hydrogen atom or a methyl group with at least one other ethylenically unsaturated monomer.

4. A gelatin layer according to claim 3, wherein said gelatin layer forms part of a photographic light-sensitive material.